US012253349B2

(12) United States Patent
Scarfe et al.

(10) Patent No.: US 12,253,349 B2
(45) Date of Patent: *Mar. 18, 2025

(54) LOAD SCANNING APPARATUS

(71) Applicant: Robotics Plus Limited, Tauranga (NZ)

(72) Inventors: Alistair John Scarfe, Tauranga (NZ); Florian Thomas Roeske, Tauranga (NZ)

(73) Assignee: Robotics Plus Limited, Tauranga (NZ)

(*) Notice: Subject to any disclaimer, the term of this patent is extended or adjusted under 35 U.S.C. 154(b) by 0 days.

This patent is subject to a terminal disclaimer.

(21) Appl. No.: 18/531,120

(22) Filed: Dec. 6, 2023

(65) Prior Publication Data
US 2024/0133675 A1    Apr. 25, 2024

Related U.S. Application Data

(63) Continuation of application No. 17/384,791, filed on Jul. 25, 2021, now Pat. No. 11,885,605, which is a continuation of application No. PCT/IB2020/050547, filed on Jan. 24, 2020.

(30) Foreign Application Priority Data
Jan. 25, 2019   (NZ) .................................. 750213

(51) Int. Cl.
*G01B 11/02*    (2006.01)
*B25J 19/02*    (2006.01)
(Continued)

(52) U.S. Cl.
CPC .......... *G01B 11/022* (2013.01); *B25J 19/021* (2013.01); *G01B 11/026* (2013.01); *G01B 11/08* (2013.01);
(Continued)

(58) Field of Classification Search
USPC .......................................................... 348/48
See application file for complete search history.

(56) References Cited

U.S. PATENT DOCUMENTS 5,307,294 A * 4/1994 Aman .................. G01B 11/002
702/128
10,586,347 B1 * 3/2020 Stroble ............... G06F 18/2431
(Continued)

FOREIGN PATENT DOCUMENTS

AU    2013237637 A1    4/2014
RU       2492477 C1    9/2013
(Continued)

OTHER PUBLICATIONS

International Search Report and Written Opinion dated Mar. 10, 2020 in connection with International Application No. PCT/IB2020/050547, 11 pages.
(Continued)

*Primary Examiner* — Stuart D Bennett
(74) *Attorney, Agent, or Firm* — Baker & McKenzie LLP

(57) ABSTRACT

A load scanning apparatus for taking physical measurements from a load. The load scanning apparatus has a scanning robot including a plurality of sensors arranged in an array spanning substantially across at least one load dimension in a first direction. The array of sensors moves together in a second direction, in a scanning plane. The plurality of sensors are configured to take images of the load from the scanning plane, and are configured to capture distance information about the distance of said load from the scanning plane.

20 Claims, 11 Drawing Sheets

(51) Int. Cl.
  *G01B 11/08* (2006.01)
  *G01B 11/28* (2006.01)
  *G01N 21/898* (2006.01)
  *G01N 33/46* (2006.01)
  *G06T 7/593* (2017.01)
  *G06T 7/62* (2017.01)
  *G08G 1/095* (2006.01)
  *H04N 13/156* (2018.01)
  *H04N 13/243* (2018.01)
  *H04N 23/695* (2023.01)
  *H04N 13/00* (2018.01)

(52) U.S. Cl.
  CPC ....... *G01B 11/285* (2013.01); *G01N 21/8986* (2013.01); *G01N 33/46* (2013.01); *G06T 7/593* (2017.01); *G06T 7/62* (2017.01); *G08G 1/095* (2013.01); *H04N 13/156* (2018.05); *H04N 13/243* (2018.05); *H04N 23/695* (2023.01); *G06T 2207/30161* (2013.01); *H04N 2013/0081* (2013.01)

(56) References Cited

U.S. PATENT DOCUMENTS

| | | | | |
|---|---|---|---|---|
| 2005/0192702 | A1* | 9/2005 | Moutsokapas | B66C 13/48 700/213 |
| 2008/0316473 | A1* | 12/2008 | Fahrenschon | G01N 33/46 356/237.2 |
| 2009/0303497 | A1* | 12/2009 | Hamalainen | G01B 11/00 356/635 |
| 2013/0144568 | A1* | 6/2013 | Palma-Amestoy | G01B 11/24 703/1 |
| 2017/0235983 | A1 | 8/2017 | Alwesh et al. | |
| 2019/0034864 | A1* | 1/2019 | Skaff | G06Q 10/087 |

FOREIGN PATENT DOCUMENTS

| | | |
|---|---|---|
| RU | 2678224 C1 | 1/2019 |
| WO | 2016200185 A1 | 12/2016 |

OTHER PUBLICATIONS

A first Office Action issued by the Russian Patent Office on Jul. 25, 2023 in connection with the corresponding Russian Patent Application No. 2021125246.

Office Action issued by the Russian Patent Office, dated Mar. 29, 2024, in connection to Russian Patent Application No. 2021-1125246, 16 pages.

An Office Action issued by the Canadian Intellectual Property Office on Apr. 19, 2024 in connection with Canadian Patent Application No. 3,127,866.

* cited by examiner

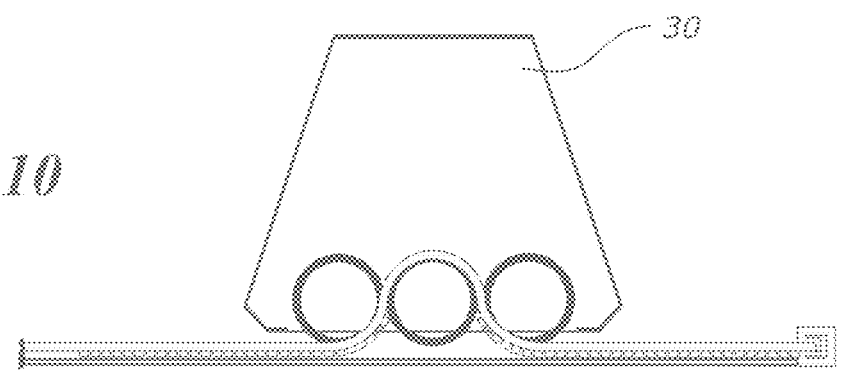
FIGURE 10
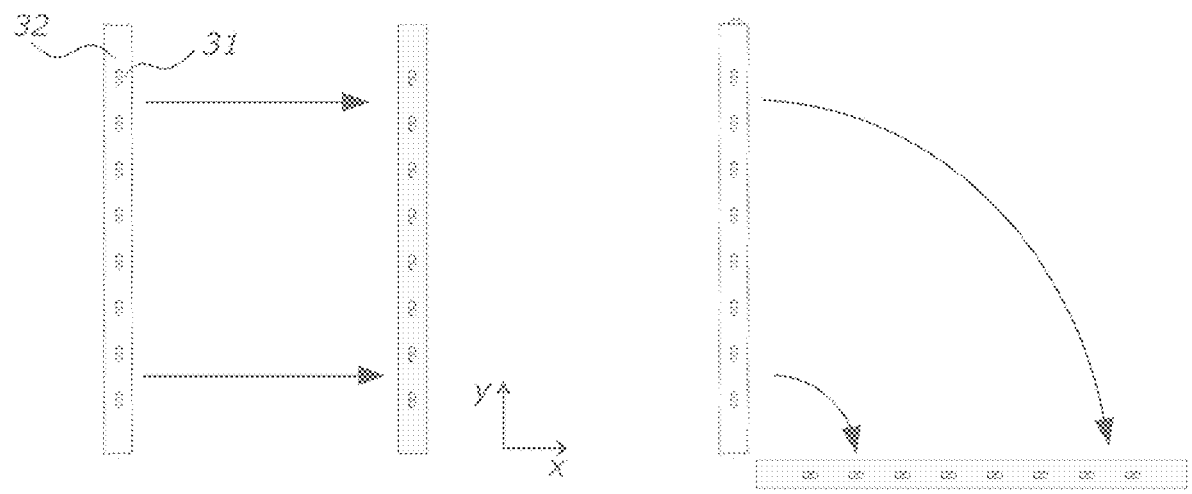
FIGURE 11
FIGURE 12
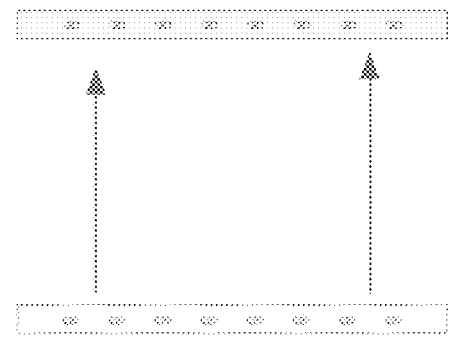
FIGURE 13

LOAD SCANNING APPARATUS

CROSS-REFERENCE TO RELATED APPLICATIONS

This application is a continuation of U.S. application Ser. No. 17/384,791, filed on Jul. 25, 2021, which is a continuation of and claims priority to International Application No. PCT/IB2020/050547, filed on Jan. 24, 2020, titled "Load Scanning Apparatus," which claims priority to New Zealand Application No. 750213, filed on Jan. 25, 2019, all of which are incorporated by reference in their entirety for all purposes.

FIELD OF THE INVENTION

The present invention relates to a load scanning apparatus and method. More particularly, but not exclusively, it relates to an autonomous load scanning apparatus for determining physical characteristics of a load of articles. More particularly still, an example of the invention relates to an apparatus and method of autonomously scanning a load of logs to determine actual and/or usable physical characteristics such as length, quality, diameter, perimeter and/or volume.

BACKGROUND OF THE INVENTION

Determining the volume of total or usable timber in whole logs is an important task in the forestry industry. The volume of usable timber determines what portion of log loads can be sold and exported and therefore the value and price of the log loads.

Traditionally, staff use rulers or other hand-held measurement tools to manually determine the physical dimensions of the logs. The physical dimensions of the logs which were obtained manually would then then be used to determine a measure of timber volume. This method of determining the volume of usable timber is slow, repetitive in nature, highly labour-intensive, and may be prone to human error. Additionally, the diameters of logs within a load may vary greatly, and often logs are not circular, therefore requiring many measurements. Furthermore, manual measuring of logs can be a dangerous operation for staff.

It may be desirable to provide equipment to determine timber volume which reduces or eliminates the need for human input which may be labour intensive or dangerous. It may also be desirable to provide timber measuring equipment which increases the efficiency of measuring a load to reduce operation costs for timber suppliers.

It is common in the timber industry for the price of a load to be calculated on some sort of bulk measurement and approximation. For example, the Japanese Agricultural Standard Measurement, among others. Some timber measuring methods require the logs to be removed from a vehicle before measurements can be taken. These methods are time and labour intensive, and also have safety issues. It may be desirable to provide timber measuring equipment which is able to measure volumes of timber without the need to remove the logs from the loaded vehicle.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

For the purpose of this specification, where method steps are described in sequence, the sequence does not necessarily mean that the steps are to be chronologically ordered in that sequence, unless there is no other logical manner of interpreting the sequence.

It is an object of the present invention to provide a log scanning apparatus which overcomes or at least partially ameliorates some of the abovementioned disadvantages or which at least provides the public with a useful choice.

BRIEF DESCRIPTION OF THE INVENTION

According to a first aspect the invention broadly comprises a load scanning apparatus for taking physical measurements from a load having load dimensions of load length, load width and load height, the apparatus comprising:
  a scanning robot including a plurality of sensors arranged in an array spanning substantially across at least one of said load dimensions in a first direction, and
  a processor for processing a collection of images taken by the plurality of sensors and stitching the collection of images together to generate a 3D representation of said load,
  wherein the array of sensors are fixed relative to each other in the first direction and moves together in a second direction, in a scanning plane,
  wherein the plurality of sensors are positioned to have a line of sight generally perpendicular to the scanning plane, and
  wherein said plurality of sensors are configured to capture the collection of images of said load from said scanning plane, and configured to capture distance information about the distance of said load from said scanning plane.

According to another aspect the load is a load of logs, arranged generally parallel to each other in a stack.

According to another aspect the plurality of sensors translates together along the load length in a longitudinal direction generally parallel to the load length.

According to another aspect the plurality of sensors rotates between a first orientation and a second orientation to face opposing faces of said load.

According to another aspect the plurality of sensors rotates 180° between the first orientation and the second orientation, to face opposite ends of said load of logs.

According to another aspect the scanning robot comprises a first set of sensors fixed in a first orientation and a second set of sensors fixed in a second orientation, to scan log faces of adjacent log packets.

According to another aspect the scanning robot is supported by two horizontally spaced apart parallel tracks.

According to another aspect the two tracks are raised and supported off a ground surface.

According to another aspect the scanning robot is a mobile scanning unit having a driving mechanism to propel itself to the load and/or self-propel itself along the load.

According to another aspect the mobile scanning unit can be manually driven by an operator or movement of the mobile scanning unit may be automated.

According to another aspect the mobile scanning unit can detect and align itself with the load.

According to another aspect the load scanning apparatus comprises multiple robot units.

According to another aspect one or more of the robot units are used to perform one or a combination of the following tasks:
a) scanning,
b) ticketing logs,
c) water blasting, or
d) labelling.

According to another aspect the multiple robot units are located along the same tracks.

According to another aspect the scanning robot is on an overhead gantry.

According to another aspect the sensors are range imaging cameras selected from one or more of:
a) stereo cameras,
b) structured light cameras
c) time-of-flight cameras, or
d) a single camera taking offset images.

According to another aspect the scanning robot comprises a cross member and the plurality of sensors are fixed on the cross member.

According to another aspect the array of sensors translates together in the second direction, the second direction being perpendicular to said first direction.

According to another aspect the cross member moves between a raised position and a lowered position on the scanning robot to scan said load.

According to another aspect the array of sensors moves together in an arc.

According to another aspect the cross member moves between a raised position and a lowered position on the scanning robot to scan said load.

According to another aspect the plurality of sensors span approximately the load width to capture a load of logs without moving the scanning robot in a traverse direction.

According to another aspect the cross member has a width between approximately 30 mm and 500 mm to fit in gaps between packets of logs in a log load.

According to another aspect the plurality of sensors moves between a raised position and a lowered position to take images from a generally horizontal perspective.

According to another aspect the plurality of sensors moves in a longitudinal direction to take top-down-view images to form a collection of images along the load length.

According to another aspect the plurality of sensors are arranged in stereo pairs.

According to another aspect the apparatus comprises 4 to 10 stereo pairs.

According to another aspect the apparatus is between 15 and 50 metres long spanning at least the load length.

According to another aspect the apparatus is between 20 and 30 metres long spanning at least the load length.

According to another aspect the plurality of sensors can be lowered 2 to 5 metres from the raised position to the lowered position to scan a stack of log ends in the load of logs.

According to another aspect the plurality of sensors can be lowered 3 to 4 metres from the raised position to the lowered position to scan a stack of log ends in the load of logs.

According to another aspect the scanning robot comprises alignment sensors to determine when the scanning robot is above the load or gaps between adjacent load packets.

According to another aspect the apparatus further comprises guide rails configured to guide a logging vehicle to a position suitable for scanning within a load receiving bay.

According to another aspect the apparatus further comprises a sensor to determine if a logging vehicle is in a position suitable for scanning.

According to another aspect the apparatus further comprises indicators to indicate to a driver of a logging vehicle to drive, slow down or stop.

According to another aspect the invention broadly comprises a system or apparatus for taking physical measurements from a load comprising:
providing a load scanning apparatus to take a collection of images, and
a processor for processing the collection of images.

According to another aspect the processor stitches the collection of images taken by the plurality of sensors to generate a 3D representation of said load.

According to another aspect the processor generates a rendered 2D stitched image or a 3D render of the load from the collection of images.

According to another aspect the processor corrects parallax/perspective error in the stitched output.

According to another aspect said load is a load of logs, and the processor processes images taken by the plurality of sensors to determine a physical characteristic of individual logs and/or the load.

According to another aspect said physical characteristic is one or more of:
i. a log diameter,
ii. a minimum log diameter,
iii. a maximum log diameter,
iv. a log area,
v. a log perimeter,
vi. a usable log perimeter,
vii. a usable log area,
viii. a log defect(s),
ix. a position of said log,
x. traceability data.

According to another aspect the load scanning apparatus measures distance data and/or log identification data.

According to another aspect the distance data is the distance between a camera position and a log face.

According to another aspect the processor scales a number of pixels in the images into physical measurements of individual logs.

According to another aspect the processor processes images taken by the plurality of sensors to determine a volume of timber from a load of logs.

According to another aspect the volume of timber is determined from a physical characteristic determined from a rendered 2D stitched or 3D image of the load, distance data and robot position data.

According to another aspect further comprising a memory configured to store data.

According to another aspect the invention broadly comprises a method for taking physical measurements from a load comprising:
providing a load scanning apparatus,
positioning a load in a load receiving bay of the load scanning apparatus,
moving the array of sensors together, and
taking a collection of images from the load to determine physical measurements.

According to another aspect the load is a load of logs, arranged generally parallel to each other in a stack.

According to another aspect the array of sensors moves from a raised position to a lowered position.

According to another aspect the array of sensors moves together in a horizontal direction from one side of the load to another side of the load.

According to another aspect the array of sensors moves together in an arc from a vertical orientation to a horizontal orientation or from a horizontal orientation to a vertical orientation.

According to another aspect further comprising moving the scanning robot along the load length in a longitudinal direction of the load.

According to another aspect further comprising detecting gaps between log packets before moving the array of sensors into the gaps between the log packets.

According to another aspect images are taken by the plurality of sensors on horizontal planes substantially perpendicular to log ends.

According to another aspect further comprising rotating the plurality of sensors to face the load of logs.

According to another aspect the array of sensors is lowered in step increments.

According to another aspect at each step increment, a series of images are taken by the array of sensors before moving to the next step increment.

According to another aspect the array of sensors translates and captures images without stopping.

According to another aspect further comprising stitching a collection of images taken by the plurality of sensors to form a 3D representation of the load.

According to another aspect further comprising forming a rendered 2D stitched image of the load from the collection of images.

According to another aspect further comprising processing images taken by the plurality of sensors to determine one or more of:
i. a log diameter,
ii. a minimum log diameter,
iii. a maximum log diameter,
iv. a log area,
v. a log perimeter,
vi. a usable log perimeter,
vii. a usable log area,
viii. a log defect(s),
ix. a position of said log,
x. traceability data.

According to another aspect the load scanning apparatus takes distance data and/or log identification data.

According to another aspect the distance data is the distance between a camera position and a log face.

According to another aspect further comprising processing images taken by the plurality of sensors to determine the volume of useable timber from a load of logs.

According to another aspect the volume of timber is determined from a physical characteristic determined from a rendered 2D stitched or 3D image of the load, distance data and robot position data.

According to another aspect the load of logs is driven into the load receiving bay by a logging vehicle and measurements are taken as the load of logs remain on the vehicle.

According to another aspect further comprising automatically detecting and reading identification codes on logs from the images.

Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification and claims means "consisting at least in part of". When interpreting statements in this specification and claims which include that term, the features, prefaced by that term in each statement, all need to be present but other features can also be present. Related terms such as "comprise" and "comprised" are to be interpreted in the same manner.

BRIEF DESCRIPTION OF THE DRAWINGS

The invention will now be described by way of example only and with reference to the drawings depicting a log scanning embodiment in which:

FIG. 10 shows a side view of a scanning robot on a belt.

FIG. 11 shows a schematic view of a scanner having a horizontally translated sensor array.

FIG. 12 shows a schematic view of a scanner having a rotated sensor array.

FIG. 13 shows a schematic view of a scanner having a vertically translated sensor array.

DETAILED DESCRIPTION OF PREFERRED EMBODIMENTS

The present invention is a log scanning apparatus 1 as shown in FIGS. 1-15 for taking physical measurements from a load of logs 2. Preferably, the log scanning apparatus 1 takes scans of log ends 3, and uses the collected data to calculate useful information about the load.

Figure 1:
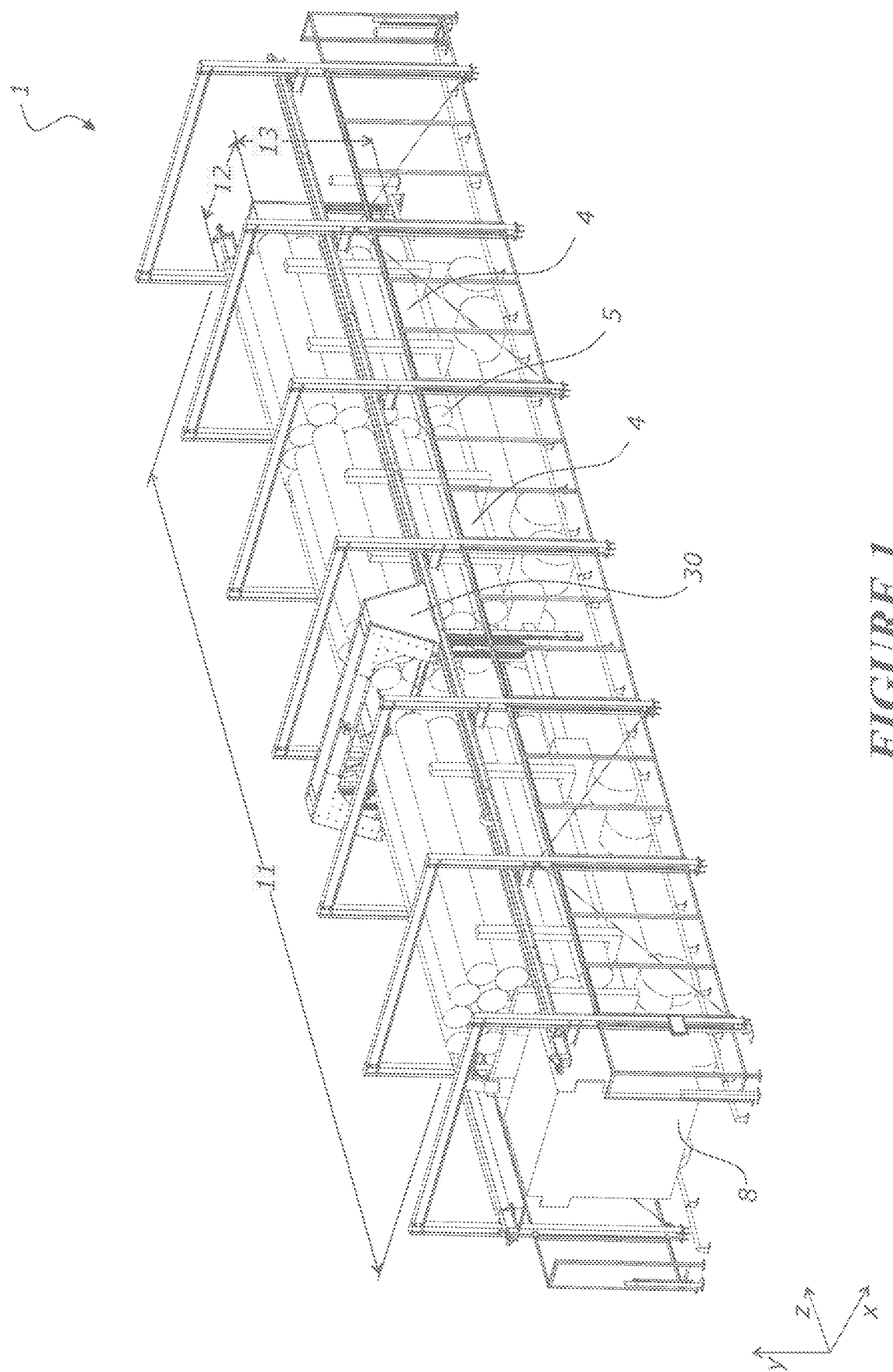
FIG. 1 shows a perspective view of a log scanning apparatus and a logging vehicle.

A load of logs 2 may be defined as a stack of logs arranged in a generally parallel bundle where the longitudinal axis of the logs in the load are substantially parallel with each other as shown in FIG. 1. In order to improve efficiency, it is preferred that the load of logs 2, are loaded onto a vehicle. However, it will be appreciated that the technology would be applicable off a vehicle.

Figure 7A:
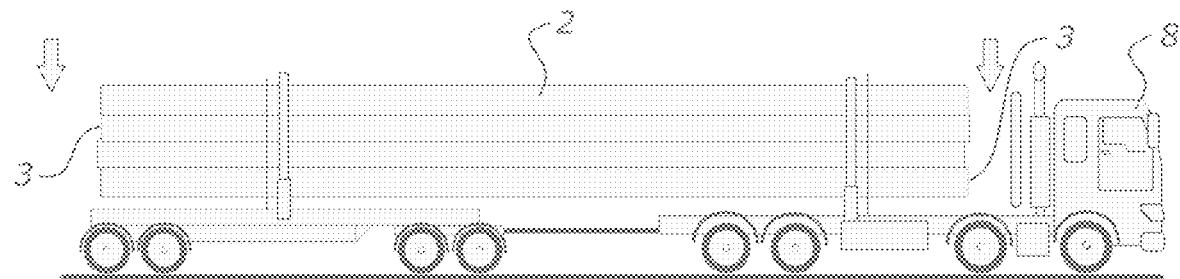
FIG. 7A-7D shows a side view of different configurations of logs on a logging vehicle.
Figure 7B:
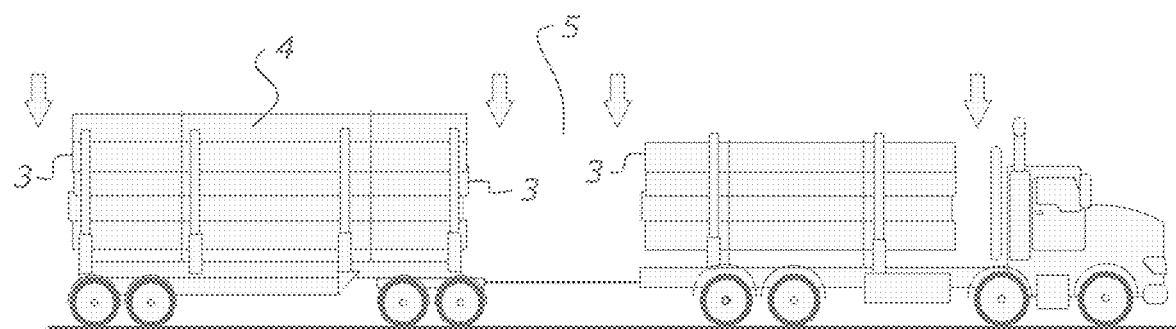
Figure 7D:
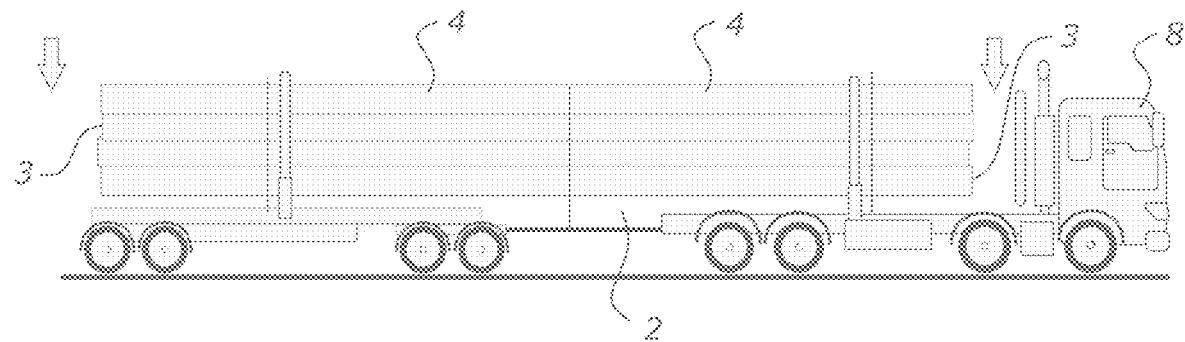
Figure 8:
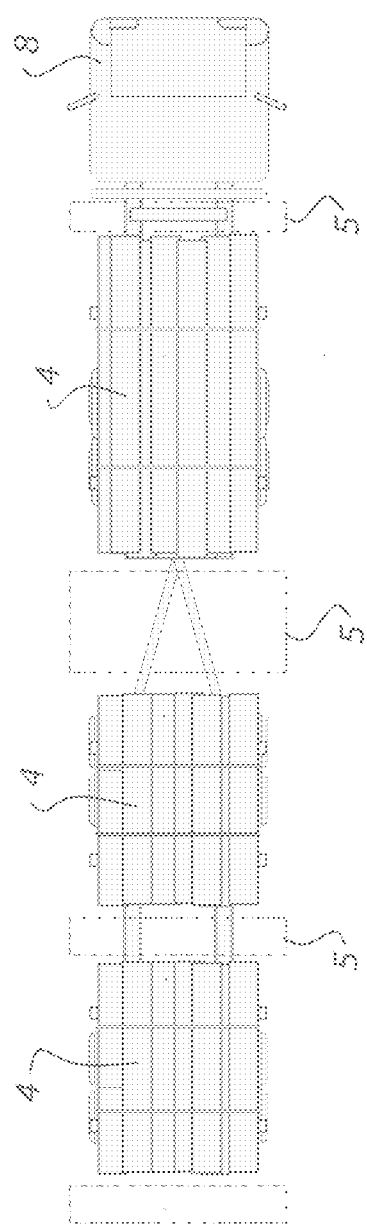
FIG. 8 shows a top view of a logging vehicle with logs.

Each load of logs 2 may include one or more packets 4 of logs. A packet 4 of logs may be identified as a single bundle of logs (FIG. 7A) or bundles of logs separated from each other in the longitudinal direction by a gap 5 (FIG. 8). Some loads 2 do not have gaps 5 between the packets 4 (e.g. where there is only one packet in the load as shown in FIG. 7A, where the loads are packed together with no gap as shown in FIG. 7D or without a substantial gap). Where there is only one packet 4 in the load 2 (or where there is no substantial gap between packets), only the outside faces of the load will need to be scanned.

With reference to FIG. 1, the load of logs 2 comprises a load length 11, a load width 12 and a load height 13. For each packet 4, there may be different packet lengths (as a result of individual log lengths), packet width, and/or packet height.

Preferably, the volume of usable timber is a physical measurement which can be estimated from images taken by the log scanning apparatus 1. The volume of usable timber in whole logs is an important physical measurement as it can help determine the value and price of a load of logs. For example, JASM (Japanese Agricultural Standard Measurement), is just one example of an estimation method that may be used to volume/value as discussed in more detail later.

A key function of the log scanning apparatus 1 may be for determining dimensions and/or volume and/or value of usable timber. However, it is anticipated that the log scanning apparatus 1 may be used for other purposes, such as counting the number of logs, identifying defects in logs, or identifying the type or species of logs for example. This might require sensors, other than imaging cameras, to be fitted to the array of sensors.

Preferably, the log scanning apparatus 1 provides an efficient, simple to use, largely automated, safe solution for determining log physical measurements. The log scanning apparatus 1 as described here is robust and can operate continuously as required to determine physical measurements from logs.

It is also anticipated, the apparatus 1 may be used to take physical measurements from other objects. The apparatus may determine physical measurements from vertical faces of a load. Scans of vertical faces may be obtained in addition to, or separate from, top and/or side views of a load.

It will be appreciated that these figures illustrate the general principles of the log scanning apparatus 1, and the invention is not limited to the precise mechanical configuration illustrated in the figures.

As shown in FIG. 1, the log scanning apparatus 1 is configured to scan and take physical measurements from a load of logs 2. To take physical measurements of a load of logs 2, for example a logging vehicle 8, the logs 2 are preferably positioned in a load receiving bay 21 of the log scanning apparatus 1.

Preferably, the physical measurements can be taken from the load of logs while the logs remain on a logging vehicle 8. It may be beneficial to take measurements of logs 2 while they remain on a vehicle 8 as removing the logs can be a time and labour intensive. Reducing the number of times logs 2 need to be loaded, unloaded and moved may also decrease the risk of injuries to workers.

In the preferred configurations, the log scanning apparatus 1 comprises a scanning robot 30.

In one configuration, the scanning robot 30 takes the form of an overhead gantry which spans across the load width 12. Preferably, the logs scanning apparatus 1 can capture scan of a load of logs 2 across its entire width without moving the scanning robot 30 in a traverse (width) direction.

For example, in one configuration the scanning robot 30 is an overhead gantry robot which moves above the load of logs in a longitudinal direction. In another alternative configuration, the scanning robot 30 may move on a side (beside) the load of logs in a longitudinal direction. Preferably, in these configurations, the scanning robot 30 only needs to move in one direction to scan the log ends, as the plurality/array of sensors 31 are arranged to substantially span the load width 12 (a first direction), and allow the sensors to view the entire load in one direction.

Preferably, the scanning robot 30 comprises a width 35 greater than the load width 12. Preferably, the scanning robot 30 is able to scan a load width between 2 and 5 metres wide. In some configurations, the scanning robot 30 can scan a load width between 2 and 4 metres wide.

In yet another configuration, the scanning robot 30 is positioned along-side the load of logs 2, rather than above. Preferably, such scanning robot 30 then spans the height 13 of the load of logs (a first direction). Preferably, in these configurations the scanning robot 30 only needs to move in one direction (in a second direction, either transverse or vertically) to scan the log ends, as the plurality of sensors 31 substantially span the perpendicular span of the load. For example, of the scanning robot 30 moves in the transverse direction, then the plurality of sensors 31 will span the height 13 of the load, and similarly if the scanning robot 30 moves in the vertical direction, then the plurality of sensors 31 will span the transverse width 12 of the load.

The scanning robot 30 having a plurality of sensors spanning across one dimension of the load of logs allows the scanning robot to reduce the directions (axes) in which the robot needs to move. Therefore, the time required to scan the whole log face will also be reduced.

In the preferred configurations, the scanning robot 30 comprises sensors 31 to capture physical measurements from the logs 2. In the preferred configurations, a plurality of sensors 31 are arranged in an array on the scanning robot 30, configured to take images of log ends 3. It is a feature of the preferred configurations that the sensors 31 are able to 'view' the log ends from a substantially perpendicular perspective.

Preferably, the plurality of sensors 31 are arranged in an array where the sensors are fixed in known positions with respect to each other. As the sensors are fixed with respect to each other, software may be used to combine/stitch the collection of images together to achieve a full image of a face of the load of logs.

Preferably, the plurality of sensors 31 are arranged in a linear array, as such an arrangement may simplify the necessary calculations and coordinate transformations used in processing. However, it will be appreciated that other sensor array configurations are achievable, and may be appropriate.

Preferably, the plurality of sensors 31 are arranged in a regular array where the sensors 31 are spaced substantially the same distance apart over the width of the load of logs. A regular array may be particularly desirable where the motion of the array of sensors is linear translation.

The plurality of sensors 31 may be arranged in a staggered array, or an irregular array. These arrangements may be more beneficial where the array of sensors moves together in an arc. In such configurations, the controller software is able to make appropriate corrections to account for the known positions of each sensor.

In the preferred configurations illustrated, the plurality of sensors 31 span at least approximately the load width 12, in order to be able to capture a scan of a load of logs 2 without moving the scanning robot in a traverse direction.

Preferably, a load of logs 2 can be scanned by moving the scanning robot 30 longitudinally, and vertically, but not in a traverse direction.

In the preferred configurations, the plurality of sensors 31 are range imaging cameras capable of measuring distance information in addition to capturing images. For example, stereo cameras, structured light cameras, time-of-flight cameras or single cameras taking offset images (to act like a stereo pair of cameras) can be incorporated into the scanning robot 30 individually or in combination to capture the necessary data from the load of logs 2. In some preferred configurations, cameras are used to capture images from multiple viewpoints to effectively form a stereo pair, capable of measuring distance information. In some alternative configurations, an array of line scanners may be used to derive additional distance information.

It is anticipated, that other cameras, or sensors known in the art which may capture the desire data may be used to scan the load of logs 2.

Preferably, the plurality of sensors 31 are arranged in an array spanning substantially across at least one of the load dimensions in a first direction (e.g. along the width 35 of the robot).

Preferably, the plurality of sensors 31 moves together in a second direction of the apparatus, in a scanning plane.

Preferably, the second direction is perpendicular to the first direction, in a scanning plane.

In one configuration, the plurality of sensors 31 translate together in a horizontal direction from one side of the load to another side of the load as shown in FIG. 11. I.e. the array of sensors spans the load height and move across the load width together.

It another configuration, the plurality of sensors 31 translate together in a vertical direction as shown in FIG. 13. I.e. the array of sensors spans the load width and move across the load height together. The array of sensors can move from a lowered position to a raised position as shown by the arrows in FIG. 13, or from a raised position to a lowered position as shown by the arrows in FIG. 3B.

Translate may be defined to mean that all the sensors 31 travel in the same direction without rotation.

It is anticipated that the array of sensors 31 can rotate together (move together in an arc) from a vertical orientation to a horizontal orientation as shown in FIG. 12, or vice versa.

In some configurations, the scanning begins after the array of sensors have moved to the desired orientation. Rotating the array of sensors may be useful to move from a stored configuration (e.g. vertical) to a configuration ready for scanning (e.g. horizontal).

In other configurations, the load is scanned as the sensors 31 move together in an arc. Once a collection of images has been taken, software can be used to stitch the images together.

Preferably, the plurality of sensors 31 translate together in a direction 'B' along the load length 11 in a longitudinal direction of the load of logs 2, generally parallel to the load length (e.g. to move to opposite log ends to achieve a complete picture of the log for timber volume calculations).

During normal operation of the log scanning apparatus 1, once the logging vehicle 8 with the logs 2 are in position, apparatus scans the logging vehicle to find the gaps 5 between the log packets. To collect data from the log ends, the scanning robot 30 moves to face a section of the load of logs 2.

The scanning robot 30 is preferably lowered, in order to view a section of the load from a substantially perpendicular position. Once the scanning robot 30 has been lowered, a collection of images of a stack of log ends 3 are taken to determine physical measurements of a load of logs 2.

As the scanning robot 30 moves along the longitudinal direction of the load of logs 2, it may be positioned above different sections of the load. A scanning robot 30 capable of moving along the load length 11 may be advantageous as images can be taken at various positions along the load of logs 2 while a logging vehicle 8 remains stationary in order to derive additional information that may be useful for various purposes. Consequently, a driver will not need to move the logging vehicle 8 while the load of logs 2 are being scanned, as the scanning robot 30 can be positioned to the desired positions as discussed later.

In other configurations, the logging vehicle 8 may be moved relative to the scanning robot 30 so that various positions along the load of logs 2 can be scanned.

The load length 11 may be determined from the distance travelled by the scanning robot 30 in the longitudinal direction overhead the load of logs 2, and/or in combination with other sensors for locating the position of the log ends.

In preferred configurations, individual log length may be determined. For example, the individual log length is determined by knowing the relative position of the sensors when they viewed each end of an individual log, and the distance from the camera to each respective end of the log.

In the preferred configurations, the plurality of sensors 31 move together in two degrees of freedom. For example, the plurality of sensors 31 translate together to along both the length 11 of the load of logs 2 and the load height 13.

In the preferred configuration, the cameras may also be rotated so that the sensors 31 can be pointed to the log faces at either end of the packet 4. Such a configuration allows the same sensor array to scan faces of the load that are oriented oppositely.

Sensors 31 may also be rotated to that they point down to scan the top of the load 2, as described above. Optionally scanning the longitudinal length of the load may provide other useful/desirable information.

Figure 3A:
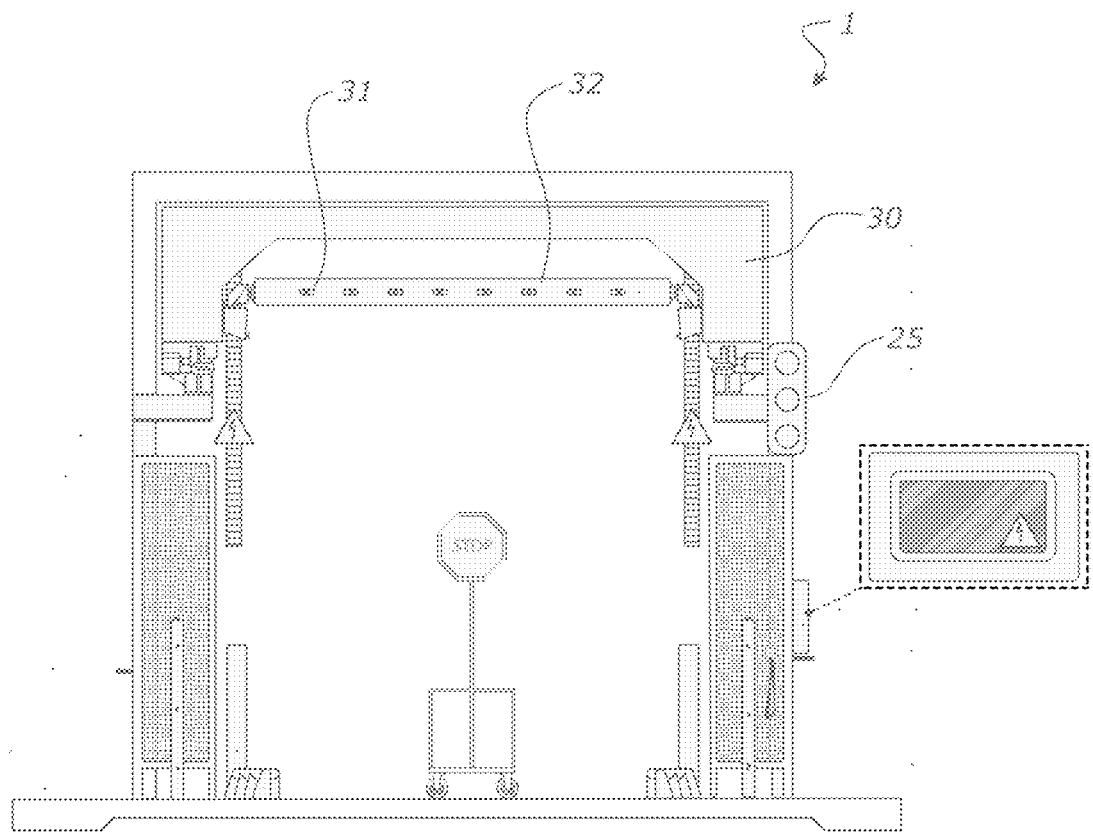
FIG. 3A shows a front view of a scanning apparatus with a plurality of sensors in a raised position.

Preferably, in the raised position as shown in FIG. 3A, the scanning robot 30 is substantially raised above the highest point of a load of logs 2.

Preferably, the scanning robot 30 can move along and above the length 11 of the load of logs 2.

A scanning robot 30 capable of moving along the length 11 of the load of logs 2 may be advantageous as only one unit is required to measure both ends of the logs. In some configurations, the log scanning apparatus 1 comprises a single scanning robot 30 to capture the physical measurements of the load of logs 2.

The scanning robot 30 preferably moves along the load length 11 in a longitudinal direction of the load of logs. In some configurations, the scanning robot 30 can move from one end of the load receiving bay 21 to the other. In other configurations, a single scanning robot 30 moves a set distance along the load receiving bay 21.

In some configurations, two or more movable scanning robots 30 may used to capture the physical measurements of the load of logs 2. Movable scanning robots 30 are still beneficial where there are multiple gantries used in the log scanning apparatus as the unit can be moved vertically to capture the entire stack of logs 2 and/or moved longitudinally along the load to the exact location for scanning while the vehicle 8 remains stationary.

In some configurations, the plurality of sensors 31 has three degrees of freedom.

Preferably, the plurality of sensors 31 on the scanning robot 30 can rotate between a first orientation and a second orientation to face a load of logs, of adjacent packets. For example, as illustrated in FIG. 7B adjacent packets may be loaded on a truck and trailer unit respectively, thus the plurality of sensors preferably rotate between a first orientation (where sensors face the rear of the truck load) and a second orientation (where the sensors face the front of the trailer load).

Preferably, the plurality of sensors 31 rotate 180° between the first orientation and the second orientation, parallel to the longitudinal direction.

In the most preferred configurations, the scanning robot 30 comprises a cross member 32. Preferably, the plurality of sensors 31 are fixed on the cross member 32.

Figure 3B:
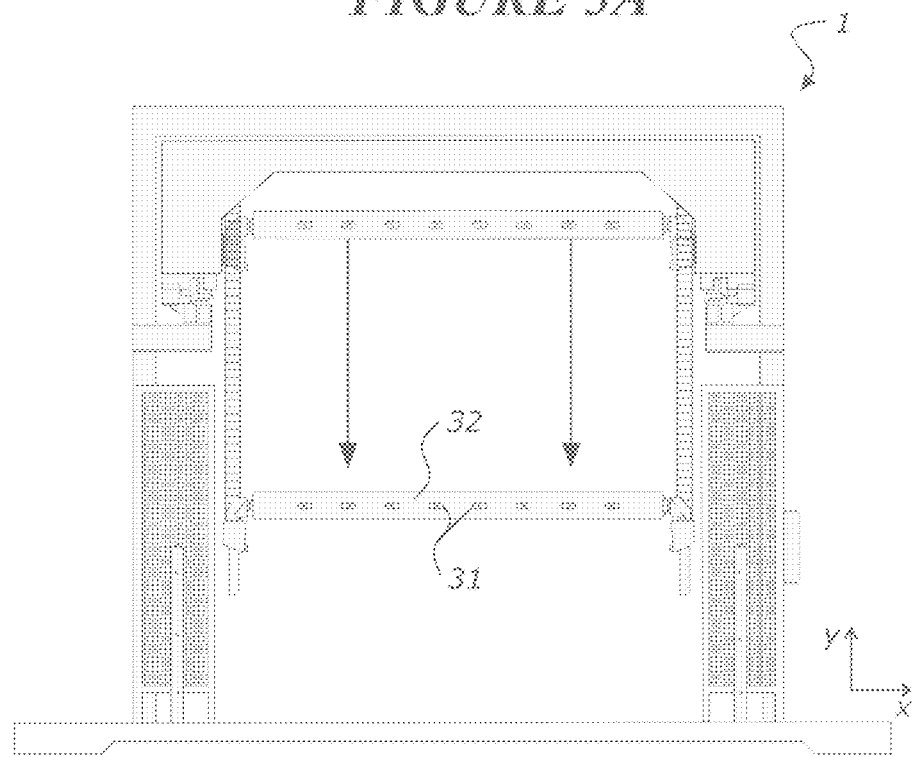
FIG. 3B shows a front view of a scanning apparatus with a plurality of sensors in a lowered position.
Figure 4:
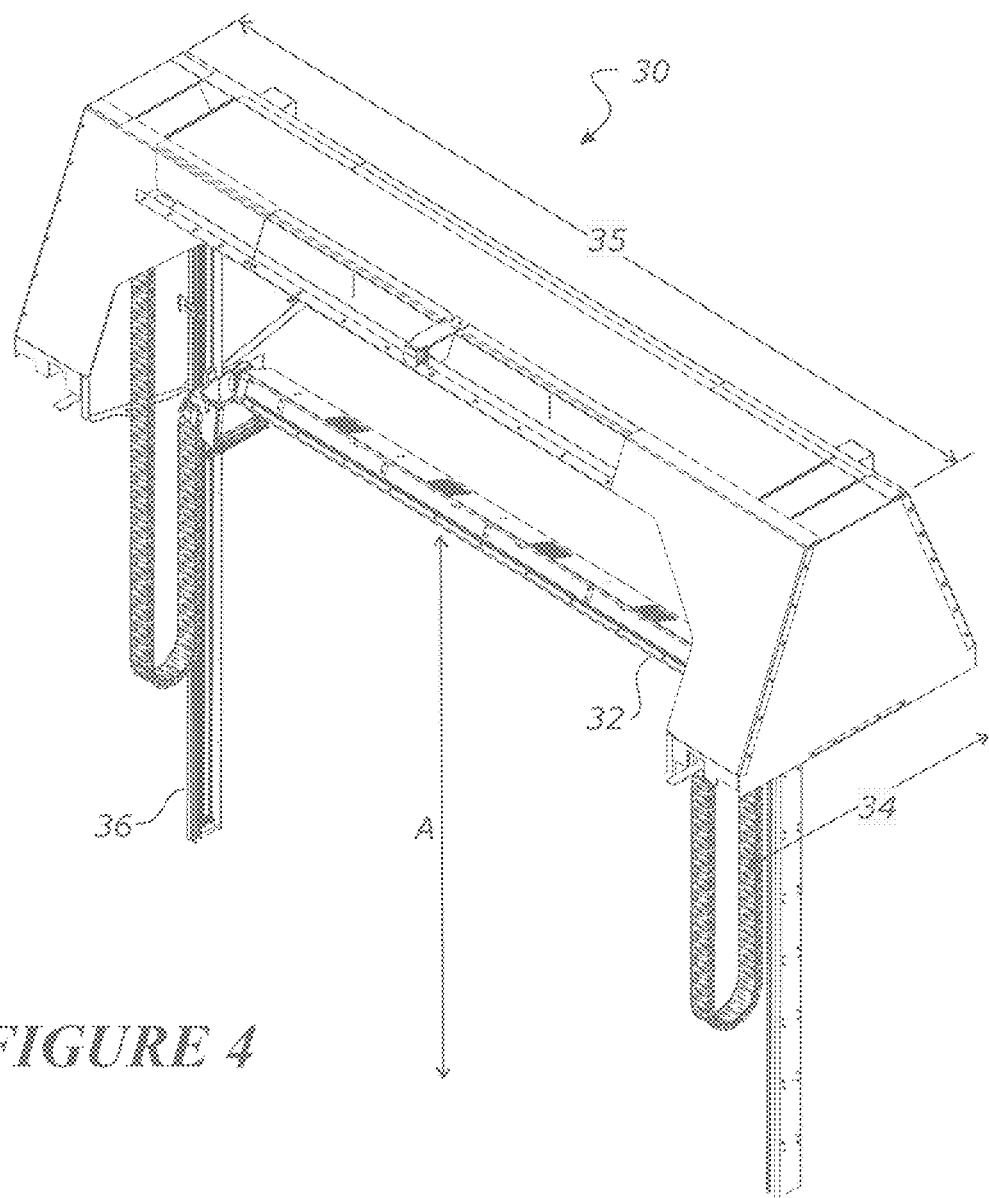
FIG. 4 shows a perspective view of a scanning robot.

Preferably, the cross member 32 moves between a raised position as shown in FIG. 3A and a lowered position as shown in FIG. 3B on the scanning robot 30 to scan a stack of log ends 3 in the load of logs 2. As the plurality of sensors 31 are located on the cross member 32, the plurality of sensors can move together in the vertical direction 'A' between the raised position and the lowered position as illustrated in FIG. 4.

Moving the plurality of cameras 31 together can significantly increase the speed of scanning times.

In some configurations, the scanning robot 30 is translated (for example, lowered) in known step increments. The scanning robots 30 in step increments allows the plurality of sensors 31 to take a series of images which represents the end faces of the load of logs 2, at known intervals which are processed later. In some configurations, a series of images are taken by the array of sensors at each step increment before moving to the next step increment.

In other configurations, the array of sensors translates (and capture images) without stopping. The scanning robot 30 can take a series of images as the cameras are moving.

A plurality of sensors 31 integrated on a cross member 32, on a scanning robot 30, may be beneficial as it simplifies the movement of the sensors relative to the logs 2 which are being scanned. When the plurality of sensors 31 are moved together, the relative positions between the sensors remain constant resulting in consistently accurate scans of log ends 3 with reduced noise and allows a substantially perpendicular to view of the end faces, which results in improved accuracy.

Optionally, the scanning robot 30 comprises a cross member guide 36. Preferably, the cross member 32 slides between a raised position and lowered position on the cross member guide 36, for moving the array of sensors 31.

Preferably, the raised position as shown in FIG. 3A is the position where the plurality of sensors is at highest point away from the ground. Preferably, in the raised position, the plurality of sensors 31 are above the top side of the logs 2, so that a logging vehicle 8 can pass under the log scanning apparatus 1.

In one configuration, the plurality of sensors are additionally able to move in a longitudinal direction to take top view images of the load of logs 2 to form a collection of images along the load length 11 in order to identify gaps and/or identify the beginning and end of each load.

Alternatively, in a preferred configuration 2D LiDAR scans the topside of the load of logs 2 in order to determine the dimensions and locate the gaps 5 between log packets 4, sufficient for moving the array of sensors into a substantially perpendicular scanning position.

As shown in FIG. 4, in the preferred configurations, the scanning robot 30 comprises a unit length 35 between approximately 3 m and 5 m.

Preferably, the scanning robot 30 comprises a unit width 34 between approximately 30 mm and 500 mm (illustrated in FIG. 4).

Preferably, the scanning robot 30 comprises alignment sensors to determine when the scanning robot is above logs 2 or gaps 5 between log packets 4.

In the preferred configurations, the apparatus 1 is between 15 and 50 metres long, spanning at least the load length 11.

In some configurations, the log scanning apparatus 1 is between 20 and 30 metres long, spanning at least the load length 11.

Figure 15:
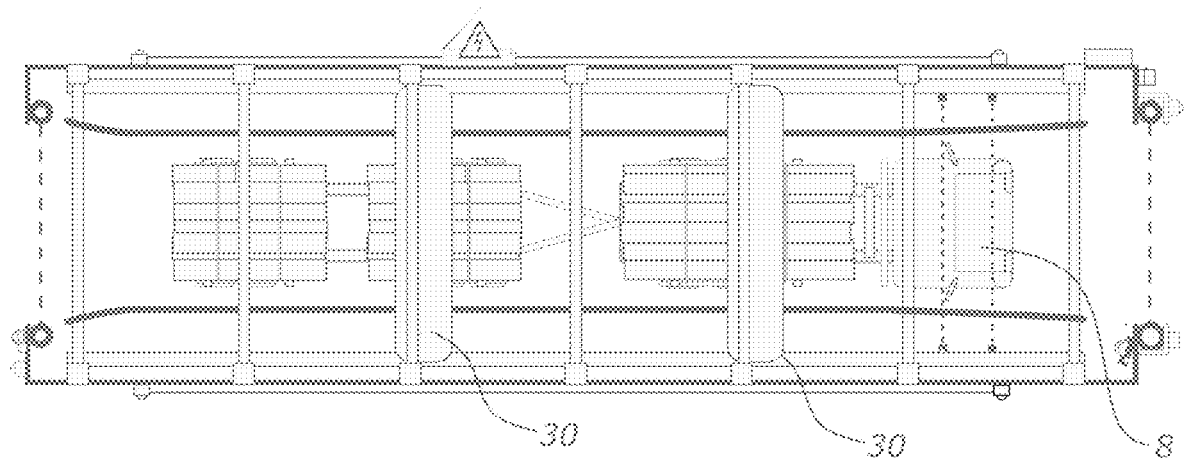
FIG. 15 shows a top view of a log scanning apparatus with multiple robot units.

In some configurations, the log scanning apparatus 1 comprises multiple robot units as shown in FIG. 15.

In some configurations, all the robot units are scanning robots 30 for scanning and taking physical measurements from the load 2. Multiple scanning robots 30 may be used to improve scanning efficiency. Scanning efficiency can be improved, as each scanning robot 30 can scan a different gap 5 between packets 4, or outside face of the load. Each scanning robot may travel a shorter distance along the length of the load 2 to scan the load, thus improving the efficiency of scanning.

In other configurations, one or more of the robot units are robots used to do tasks other than scanning such as ticketing logs, water blasting, labelling etc.

Each robot unit can move along the longitudinal axis of the load of logs 2 (Z) to scan or service the logs. In the preferred configuration, the multiple robot units are located along the same tracks 18.

In other configurations, the multiple robot units are located along independent tracks (not shown). Each scanning robot can scan or service a defined segment of the load of logs. For example, one robot unit can operate towards a front end of the logging vehicle, while another robot unit can operate towards a back end of the vehicle.

In the preferred configurations, the log scanning apparatus 1 can detect gaps 5 between log packets 4 before moving the scanning robot 30 into the gaps between the log packets. Moving the scanning robot 30 into gaps between log packets 4 may be advantageous so that log ends 3 which do not face the ends of the load may be scanned. Often multiple packets 4 of logs are transported on logging vehicles.

FIGS. 7A, 7B, 7C and 7D show a number of different loading configurations of logs 2.

FIG. 7A illustrates a load of logs 2 with a single packet 4. The log ends 3 at each end of the log load can be scanned.

FIG. 7B illustrates a load of logs 2 with two packets 4 of logs. The arrows show the gaps 5 which the scanning robot 30 can be lowered into, to take scans of log ends 3 of each packet 4.

Figure 7C:
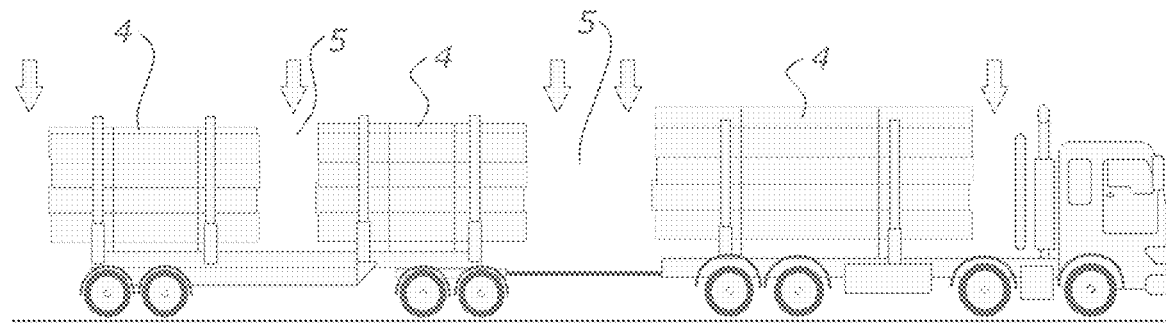

FIG. 7C illustrates a load of logs 2 with three packets 4 of logs. Once again, the arrows show gaps 5 which the scanning robot 30 can be lowered into, to take scans of log ends 3 of each packet 4.

FIG. 7D illustrates a load of logs 2 with two packets 4 of logs, generally known as "butte stacked". There is no gap 5 between the packets 4 of logs.

In some configurations, two packets 4 of logs 2 share the same gap 5 in a load of logs 2. As the scanning robot 30 is moved into the gap 5 between two packets 4, the plurality of sensors 31 scan a first packet 4 of logs where the plurality of sensors 31 are facing in a first orientation/direction. The log ends 3 are scanned as the scanning robot 30 is moved between the logs. The plurality of sensors 31 may then rotate to a second orientation and face a second neighbouring packet 4 of logs. Preferably, the neighbouring log ends 3 are scanned as the scanning robot 30 is moved out from between the logs.

In other configurations, the scanning robot 30 conducts multiple vertical sweeps to scan the different packets 4 of logs.

In alternative configurations, two sets of sensors 31 on the scanning robot 30 may be provided with one set fixed in a first orientation, and the other set fixed in a second orientation. Sensors 31 facing different orientations may be beneficial such as when scanning log ends 3 located in a gap between packets 4, and a single pass will be sufficient to scan the log faces in adjacent packets 4 simultaneously.

In the preferred configurations, component(s) of the scanning robot 30 are sized and configured to fit into narrow gaps 5 between log packets 4.

In the preferred configurations, the plurality of sensors 31 can be lowered 2 to 5 metres from the raised position to the lowered position to scan a stack of log ends 3 in the load of logs 2.

In one configuration, as shown in FIG. 4, the plurality of sensors 31 are located on the cross member 32 which can be moved alongside the log faces to scan the load of logs. The cross member 32 in one configuration is lowered to scan the log faces. In another configuration the cross member 32 is moved transversely across the log faces to scan the load.

Preferably, the cross member 32 is relatively narrow to fit into gaps 5 between the log packets 4 as illustrated in FIG. 8. For example, cross member 32 may be approximately 100 mm to 200 mm across, and have relatively compact sensors 31 attached, allowing effective scans in a gap 5 between loads down to approximately 500 mm.

In the most preferred configurations, the plurality of sensors 31 can be lowered 3 to 4 metres from the raised position to the lowered position to scan a stack of log ends 3 in the load of logs 2. Preferably, a sensor (such as LiDAR or other suitable technology) is used to detect the gaps 5 in order to determine how far to lower the cross member 32 in order to avoid collisions. It may also be preferable to include secondary sensors (such as light beam/curtains etc), sensing obstacles in the movement path of the cross member 32 in order to ensure that the cross member 32 does not collide.

In some configurations, the plurality of sensors 31 are moved across the log faces from one side to the opposite side in a traverse direction.

Preferably, the distance between the raised position and the lowered position is greater than the load height 13, so that an entire face of the load of logs 2 can be scanned by the log scanning apparatus 1 moving in direction A.

In some alternative configurations, the plurality of sensors 31 may independently depend from the scanning robot (not integrated into a single cross member), however the plurality of sensors 31 in this configuration still move together in the vertical direction 'A' from a raised position to a lowered position as associated actuator(s) move the sensors in a vertical direction by the same distance. In some configurations, one actuator controls all movement of the sensors 31 in the vertical direction. In other configurations, a plurality of actuators control movement of sensors 31 in the vertical direction.

In the preferred configurations, the plurality of sensors 31 are positioned to have a line of sight generally parallel to the longitudinal axis of the load of logs 2, and therefore generally perpendicular to the end faces of the load of logs 2.

In the most preferred configurations, the images are taken from a horizontal perspective, and substantially perpendicular to log ends 3. Preferably the plurality of sensors 31 moves between the raised position and the lowered position to take a series of images on the horizontal planes substantially perpendicular to log ends 3.

The images taken by the plurality of sensors 31 preferably forms a collection of images of the log ends 3 of the entire load.

Lowering the plurality of sensors 31 to horizontal plane substantially perpendicular to log ends 3, allows the sensors to be aimed at the log ends face on. Aiming the sensors 31 substantially perpendicular to the faces of the log ends 3 is preferable over aiming sensors at an angle relative to the faces of the log ends, which can introduce a significant parallax error, and/or result in parts of the load been obscured entirely.

Being able to capture images of log ends 3 perpendicularly, as the plurality of sensors 31 are lowered to the appropriate vertical height, ensures that logs which are recessed (i.e. set back relative to other logs) can be scanned accurately. In any given load of logs 2, some logs can be protruding, and some logs may be recessed 2' as illustrated in the schematic of the FIG. 5. Protruding logs 2 may obstruct the scanning region 33 of the sensors 31. Moving the plurality of sensors 31 to the level of each log end 3 can help ensure a full, accurate image of log ends 3 is captured.

Figure 5:
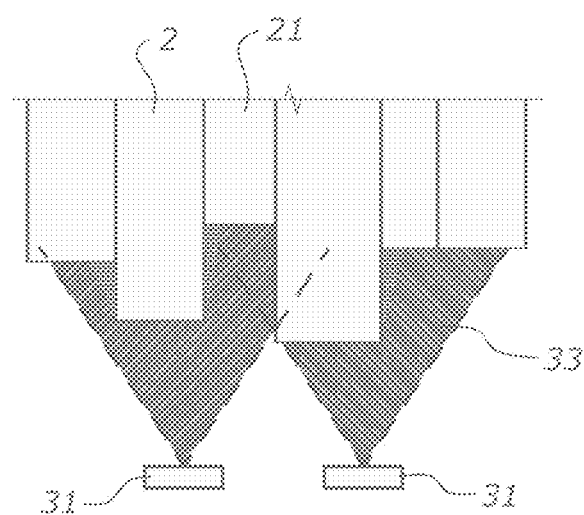
FIG. 5 shows a schematic of field of view of sensors.

Lowering plurality of sensors 31 to the desired vertical height to capture images of log ends 3 perpendicularly, may also be advantageous where the view of log ends may be obstructed by neighbouring packets 4 of logs. Log packets 4 are defined as groups of logs on the same logging vehicle 3 which may be separated along the length of the vehicle as best illustrated in FIGS. 7B and 7C. As shown in FIG. 5, having multiple sensors 31 can reduce the area of obstruction due the presence of staggered logs. Logs may be staggered due to varying log length or different stacking positions.

To determine the JASM (Japanese Agricultural Standard Measurement) system the perpendicular diameter of each log needs to be determined from the captured data. It will be appreciated that other measurement systems are suitable, but it is anticipated that all alternative systems will likely use a measure of at least one log face diameter, area, or other physical measurement and therefore benefit from the present system. The volume of timber from the load of logs 2 is estimated/determined from the diameter and length of individual logs.

Alternatively, the present system may also find utility in scanning loads of granulated material, such as wood pulp (from the top of the load), rather than packets of logs. In such a system, the array of sensors 31 and controller produce a contour map of a surface of the load. Using information from the measured the contour levels of the load, and known information about the shape of the load container, effective estimate/measurement of load volume can be obtained.

For example, to determine the volume of logs 2 which are less than 6 metres long, the following (JASM) formula may be used:

$$V = \left(D^2 * \frac{L}{10000}\right)$$

where V=volume in m³, D=shortest diameter and L=length.

To determine the volume of logs 2 which are greater than 6 meters long, the following (JASM) formula may be used:

$$V = \left(D + \frac{[L' - 4]}{2}\right)^2 * \frac{L}{10000}$$

where V=volume in m³, D=shortest diameter, L=length, and L'=length rounded to the nearest whole number in metres.

It is anticipated that other data such as area of a log end, uniformity of shape of the log, and waste area of logs, diameter, and perimeter etc may be determined from the scanned images. Traceability data to determine the history of a log may also be determined from the scanned images. For example, the 'fingerprint' of the logs can be taken from the logs by analysing the rings visible on the log faces.

Standards other than the JASM system mentioned may be used to identify timber volume, or other physical measurements from the log loads 2.

Physical measurements such as the area, diameter or volume of a log can be determined from rendered 2D stitched or 3D images of the log from the collection of images. The volume of timber can be determined from a rendered 2D stitched image of both ends of the packet of logs, distance data and robot position data. Physical measures can also be determined from 3D data.

Distance data, log identification and robot position data can be used to determine which log(s) are in the image, and the length of the logs.

Preferably, the flesh of each log 2 is used to determine the diameter of the logs 2. Preferably, the flesh of logs 2 is defined as the region excluding the bark.

In the preferred configurations, the plurality of sensors are arranged in stereo pairs as best illustrated in FIGS. 3A and 3B. Cameras arranged in stereo of pairs may be used in measuring physical dimensions of loads of logs 2, and are able to capture 3D representations of the load from the collection of images.

Preferably, the processor generates a rendered 2D stitched image or a 3D render of the load from the collection of images.

Preferably, the log scanning apparatus measures distance data. The distance data may be the distance between a camera position and a log face. It is anticipated that other distance data can be measured such as the distance from the camera position to a point on the object being scanned.

Preferably, the log scanning apparatus measures identification data to identify which log is in the image. This data can be used to correlate data from two opposing ends of the log, or simply identify which physical characteristics belong to each log.

Using stereo cameras may be advantageous as they are able to provide fast results. However, it is anticipated that any camera or sensor can be used to determine the physical dimensions and distance information of the logs, such as time of flight and projection cameras.

In the preferred configurations the log scanning apparatus 1 comprises 4 to 10 stereo pairs. In one configuration, the log scanning apparatus 1 comprises 8 stereo pairs as shown in FIGS. 3A and 3B.

Images of opposite ends of the logs can be matched up using software identification methods. For example, the 3D representations are positioned in space relative the vehicle 8. The relative positions can determine which log data is being processed.

Identification markings can be sprayed or attached onto the ends of the logs to determine which log is being looked at. This may be useful to match up log end images especially if logs cross over within a load for example.

In the preferred configurations, a processor is included in the system to process the collection of images obtained from the plurality of sensors 31.

Figure 6A:
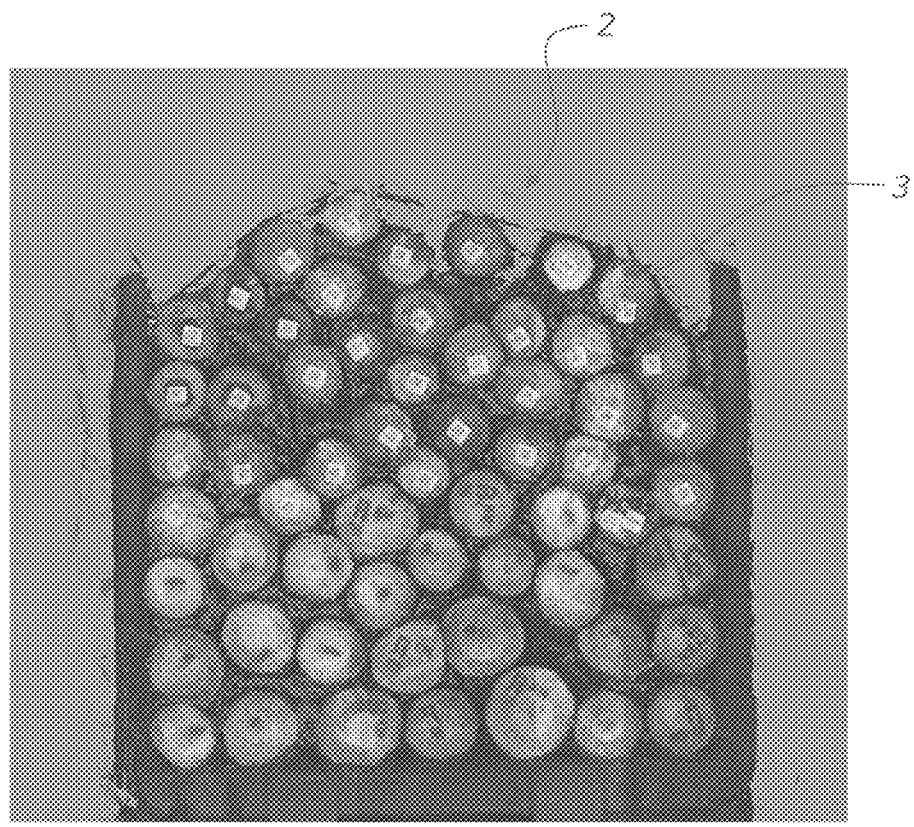
FIG. 6A shows a scanned and rendered image of log ends.

The processor preferably combines/stitches the collection of images together to obtain a full image of a face of the log load 2 as shown in FIG. 6A. Furthermore, stitching the collection of images together may be advantageous as it can significantly reduce the noise which may be present in individual images. Further still, it is preferred that the processor software corrects parallax distortion, and integrates distance measurement in order to build a 3D image.

It is also advantageous as it allows the load to be seen in its entirety. For example, data from only a part of a log may be scanned in one image, and therefore another image is required to be able to measure the entire log.

The images are stitched together by combining multiple images together. The 3D positions of the sensors/cameras 31 can be calibrated, for example to allow accurate calculation of scale and/or to convert measurements to a single global coordinate system. This allows a single coordinate space for all cameras, which is preferred. The 3D points of each camera are then mapped from one camera to any other camera in the array.

Preferably, the processor also uses the combined image to determine desired characteristics of the load such as, location of individual logs, number of individual logs, the diameter of individual logs, perimeter, area, maximum diameter, minimum diameter, and/or identify defects etc, in each individual log. The load scanning apparatus may also scan and identify the contour or the particular profile of a load. For example, contour information may be used to determine the fill level or volume of an article on a vehicle.

Figure 6B:
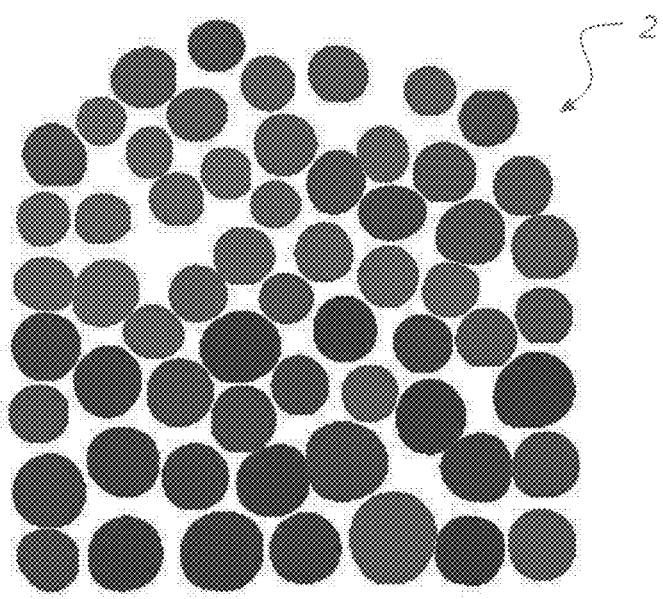
FIG. 6B shows a resulting image mask by a machine vision system of the useable log faces.

In some configurations, the processor stiches the collection images taken by the plurality of sensors 31 together to form a 3D model of the load of logs. Preferably, a series of images are collected from the plurality of sensors 31 to form a full image or model of the load of logs as illustrated in FIG. 6A. A render can be created from the full image or model as shown in FIG. 6B. To create the render, distortion (such as perspective distortion) can be removed from the viewing angle.

For example, the processor may identify the perimeter of an individual log and count the number of pixels within the perimeter to calculate an area.

In the preferred configurations, the processor processes images taken by the plurality of sensors 31 to determine the volume of the individual logs and/or load (e.g. JASM) of useable timber from the load of logs 2.

Preferably, the system includes memory configured to store data. For example, data of individual loads of logs can be used for tracking and traceability and may passed on to the operators of other processes that the logs may experience later in a supply chain.

Figure 2:
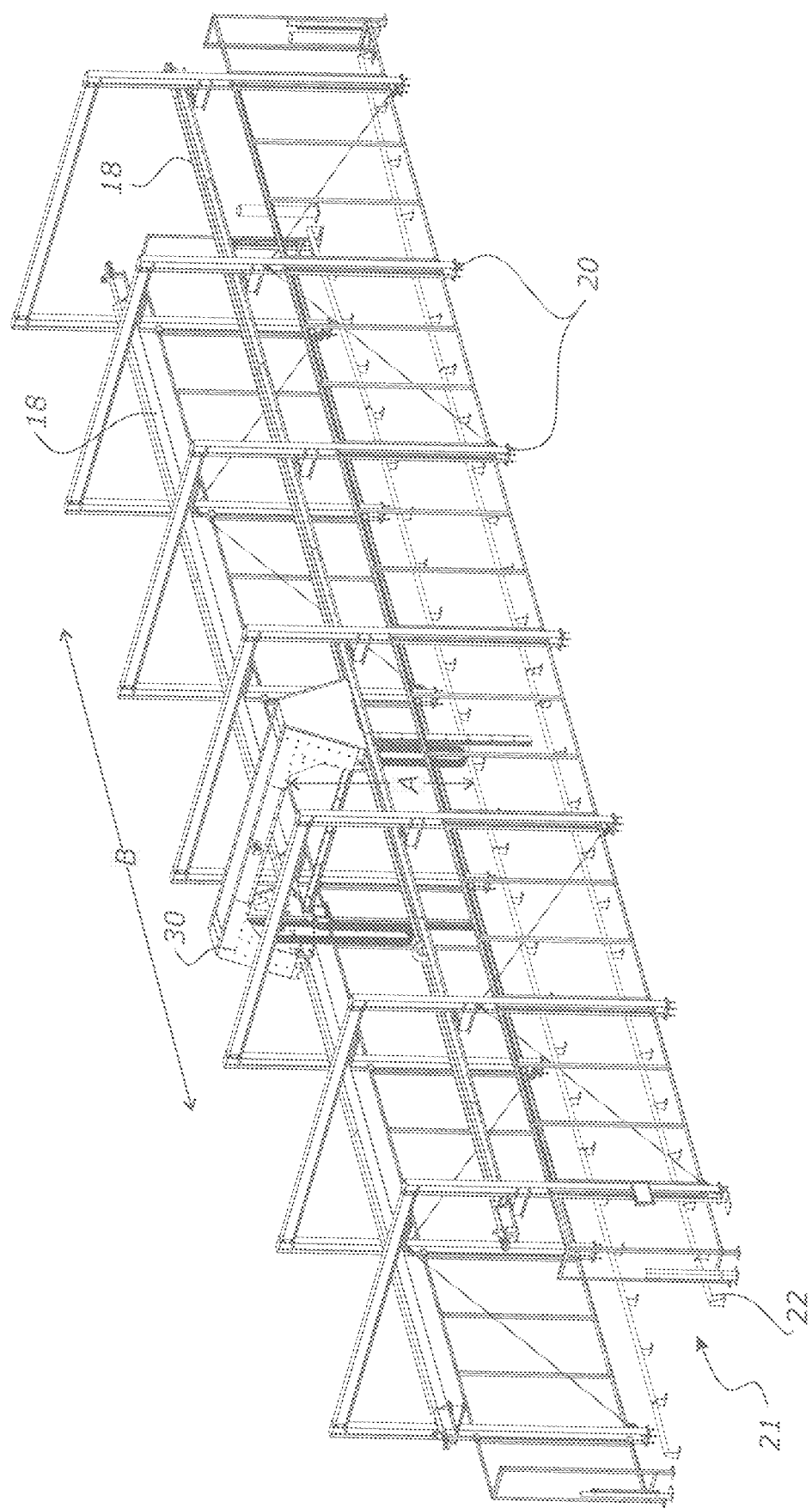
FIG. 2 shows a perspective view of the log scanning apparatus.

In one configuration, the log scanning apparatus 1 comprises two horizontally spaced apart parallel tracks 10 as referenced in FIG. 2. Preferably, the two tracks 18 are supported by support posts 20.

In some configurations, the two tracks 18 are raised and supported off the ground surface. In other configurations, the two tracks 18 are located on the ground surface, and the scanning robot 30 comprises legs to raise it above the load of logs 2.

In another configuration, the log scanning apparatus 1 comprises one track located on one side of the logging vehicle 8. The scanning robot 30 can lower the plurality of sensors 31 from one side.

As shown in FIG. 10, the scanning robot 30 optionally travels along a belt. In one configuration, the scanning robot 30 pulls itself along a toothed belt to translate along the track. It is anticipated other mechanisms may be incorporated for scanning robot to move along the track.

In some configurations, the scanning robot 30 is supported by a crane.

In another configuration, the scanning robot 30 is supported by a robotic arm. Preferably, the robotic arm moves along the length of the logging vehicle 8. The robotic arm moves the plurality of sensors 31 along and scan the log faces.

In some configurations, the scanning robot 30 is a mobile scanning unit which has a driving mechanism to propel itself to the load 2. A mobile scanning robot 30 can move to different locations (i.e. the scanning robot 30 does not have a fixed scanning location). A mobile scanning unit can drive or be driven to the load on a vehicle e.g. trains or trucks for example. The mobile scanning unit may also scan logs which are not on a vehicle, e.g. a pile of logs on the ground. It should be appreciated in these configurations, the load being scanned does not need to be transported to the load scanning apparatus at a particular scanning location, instead the mobile scanning unit can move to the load.

Figure 14:
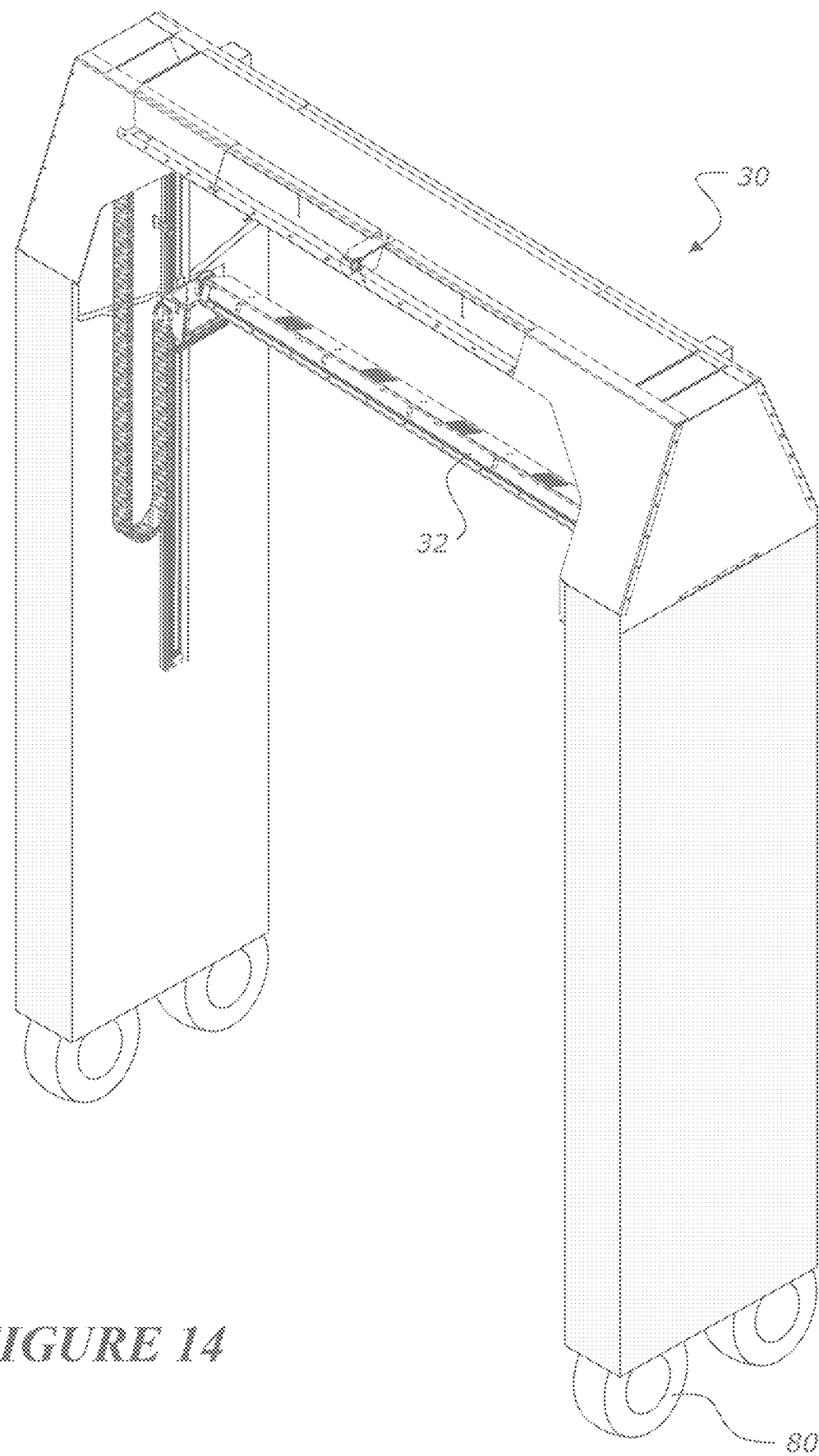
FIG. 14 shows a perspective view of a scanning robot with drive wheels.

Preferably, the driving mechanism is drive wheels 80, as shown in FIG. 14 to propel itself along the ground. It is anticipated, other mechanisms to self-propel the mobile scanning unit known to a person skilled in art may be used.

In these configurations, the mobile scanning unit 30 effectively moves along 'virtual rails,' where the movement of the scanning unit is not confined by physical tracks or rails. The mobile scanning unit 30 may move or be driven along a non-defined path (as it is not confined by tracks/rails).

The mobile scanning unit 30 may be manually driven by an operator to the load 2 (may be remote controlled), or the movement of the mobile scanning unit may be automated. For example, the mobile scanning unit 30 can detect and align itself with the load.

The mobile scanning robot 30 may also self-propel itself along the length of a vehicle 8 (along the Z direction).

Like the configurations described above, the mobile scanning unit 30 can be located towards the ground, raised overhead or supported on a side.

Optionally, the log scanning apparatus 1 comprises vehicle guides 22 configured to guide the logging vehicle 8 to a position suitable for scanning within a load receiving bay 21. In some configurations, the vehicle guides 22 are a pair of guide rails configured to guide the logging vehicle 8 within a scanning region as shown in FIGS. 1 and 2. Additionally vehicle guides 22 can help reduce the likelihood of drivers driving too close to the side components of the log scanning apparatus 1 and causing damage.

In other configurations, the vehicle guides 22 are markings on the floor to show where the area the driver should drive within for scanning. It is anticipated other means of guiding the logging vehicle 8 to a desired scanning area may be incorporated with the log scanning apparatus.

Figure 9:
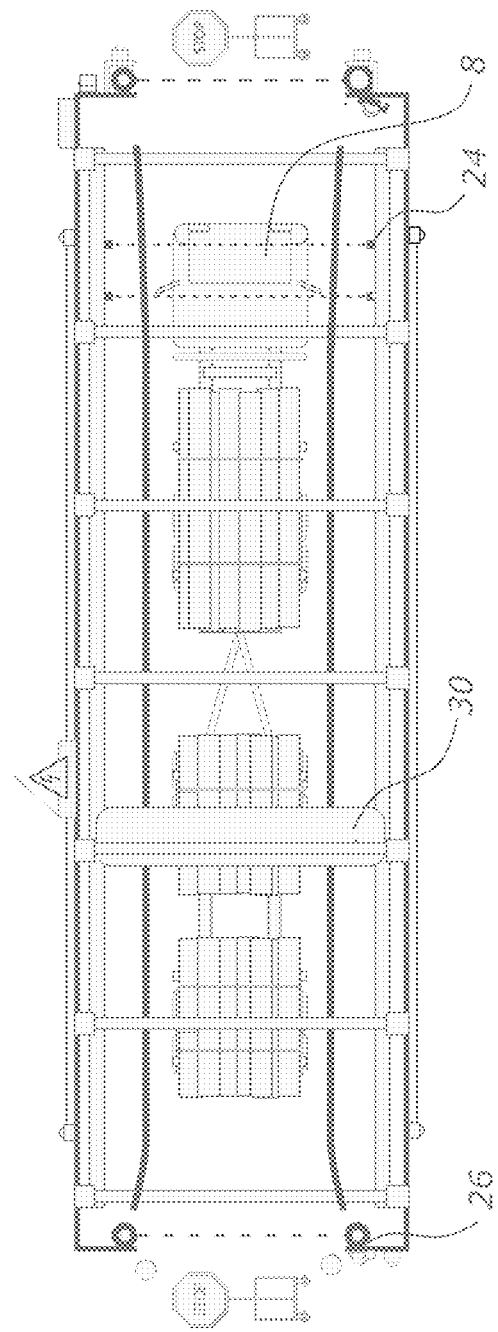
FIG. 9 shows a top view of the log scanning apparatus.

In the preferred configurations, the log scanning apparatus 1 further comprises a position sensor 24 to determine if a logging vehicle is in a position suitable for scanning as illustrated in FIG. 9.

Preferably, the log scanning apparatus 1 includes a number of safety features to prevent people from entering the load receiving bay 21 while the apparatus is operating. Optionally, the log scanning apparatus 1 comprises side barriers 23 along the length of the log scanning apparatus 1. The side barriers 23 are best shown in FIGS. 1 and 2. Preferably, the side barriers 23 prevents workers from entering the load receiving bay 21 within the log scanning apparatus for safety. The side barriers 23 may be a barrier comprising bars, wires, mesh or the like. Alternatively, light curtains may be used instead of side barriers to detect if a person has entered the workspace. If a person has entered the workspace, the machine may automatically switch off preventing further movement and/or alarms sound.

Optionally, the log scanning apparatus 1 comprises safety features to stop the apparatus from operating if a person is detected in close proximity during operation. For example, the log scanning apparatus 1 may include safety light curtains 26 as illustrated in FIG. 9. Safety light curtains may be included at the load receiving bay 21 entrance and/or exit. The light curtain emits a light beam when the apparatus 1 is in operation. If a person walks through the light curtain, the light beam is interrupted and the apparatus 1 is disabled.

Safety features are important with the log scanning apparatus 1 as it involves moving parts and components are large.

Optionally, the scanning apparatus 1 further comprises indicators 25 to indicated to a driver of a logging vehicle 8 to drive, slow down or stop. Optionally, the log scanning apparatus 1 automatically detects and reads identification codes, such as QR codes on the logs 2 from the images as shown in FIG. 6A. The QR codes can be used to determine which logs were part of the load processed, and associate the measured physical measurements with individual logs.

To those skilled in the art to which the invention relates, many changes in construction and widely differing embodiments and applications of the invention will suggest themselves without departing from the scope of the invention as defined in the appended claims.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention claimed is:

1. A load scanning apparatus for taking physical measurements from a load on a vehicle, the load comprising a first packet of logs and a second packet of logs, and the load having dimensions of load length, load width, and load height, the load scanning apparatus comprising:
    a scanning robot comprising:
        a cross member to which an array of sensors is coupled,
            wherein the array of sensors is fixed relative to each other in a first direction and are configured to move together in a second direction in a scanning plane,
            wherein the array of sensors is positioned to have a line of sight perpendicular to the scanning plane relative to at least log ends of the first packet of logs,
            wherein the array of sensors spans across at least one dimension of the load in the first direction,
            wherein the array of sensors is configured to capture a collection of images of the load from the scanning plane, and configured to capture distance information about a distance of the load from the scanning plane, and
        at least one of:
            the cross member moves between a raised position and a lowered position on the scanning robot to scan the load, and
            the cross member has a width configured to fit in a gap between:
                the first packet of logs, and
                the second packet of logs; and
    a processor configured to:
        process the collection of images taken by the array of sensors, and
        stitch the collection of images together to generate a 3-dimensional (3D) representation of the load.

2. The load scanning apparatus of claim 1, wherein:
the scanning robot is moved into the gap to scan log ends of the first packet of logs based on a first orientation of the scanning robot; and
the array of sensors of the scanning robot is rotated within the gap to cause the scanning robot to be in a second orientation and thereby enable scanning log ends of the second packet of logs.

3. The load scanning apparatus of claim 1, wherein:
the array of sensors of the scanning robot is configured to have a first orientation;
the scanning robot comprises a set of sensors that is different from the array of sensors such that the set of sensors is configured to have a second orientation; and
a single pass of the scanning robot within the gap enables scanning of:
log ends of the first packet of logs by the array of sensors, and
log ends of the second packet of logs by the set of sensors that is different from the array of sensors.

4. The load scanning apparatus of claim 1, wherein the array of sensors comprises at least one LiDAR sensor configured to detect the gap between the first packet of logs and the second packet of logs and thereby determine how far to lower the cross member.

5. The load scanning apparatus of claim 1, wherein the array of sensors comprises a sensor configured to detect an obstacle in a movement path of the cross member.

6. The load scanning apparatus of claim 1, wherein a distance between the raised position and the lowered position is greater than the load height.

7. The load scanning apparatus of claim 1, wherein the array of sensors moves between the raised position and the lowered position to capture the collection of images of the load at a horizontal plane substantially perpendicular to log ends of at least the first packet of logs.

8. The load scanning apparatus of claim 1, wherein:
the first packet of logs comprises logs that are arranged in parallel relative to each other; and
the second packet of logs comprises logs that are arranged in parallel relative to each other.

9. The load scanning apparatus of claim 1, wherein the scanning robot is configured to perform one or more of:
(a) scanning;
(b) ticketing logs;
(c) water blasting; and
(d) labeling.

10. The load scanning apparatus of claim 1, wherein at least one of:
the array of sensors translates together in the second direction, the second direction being perpendicular to said first direction; and
the array of sensors moves together in an arc.

11. The load scanning apparatus of claim 1, wherein the cross member has a width between 30 mm and 500 mm.

12. The load scanning apparatus of claim 1, further comprising one or more of:
alignment sensors that determine when the scanning robot is above the load or gaps between the first packet of logs and the second packet of logs;
guide rails configured to guide a logging vehicle to a position suitable for scanning within a load receiving bay;
a sensor that determines if a logging vehicle is in a position suitable for scanning;
indicators that indicate to a driver of a logging vehicle to drive, slow down or stop; and
a memory configured to store data.

13. The load scanning apparatus of claim 1, wherein at least one of
the processor is configured to generate one of
an image of the load based on a stitched collection of images, or
a 3D image of the load based on the stitched collection of images;
the processor is configured to correct a parallax or a perspective error comprised in the stitched collection of images;
the processor is configured to process images taken by the array of sensors to determine one or more physical characteristics of at least one of an individual log comprised in the load and the load;
the processor is configured to scale a number of pixels in the collection of images into physical measurements of individual logs; and
the processor is configured to process images taken by the array of sensors to determine a volume of timber from the load.

14. The load scanning apparatus of claim 1, wherein:
the processor is configured to process images taken by the array of sensors to determine one or more physical characteristics of at least one of an individual log or the load; and
the one or more physical characteristics comprises one or more of:
a log diameter,
a minimum log diameter,
a maximum log diameter,
a log area,
a log perimeter,
a usable log perimeter,
a usable log area,
a log defect,
a position of said log, and
traceability data.

15. The load scanning apparatus of claim 1, wherein
the load scanning apparatus is configured to measure one or more of distance data and log identification data; and
the distance data is a distance between a camera position and a log face.

16. The load scanning apparatus of claim 1, wherein
the processor is configured to process images taken by the array of sensors to determine a volume of timber from the load; and
the volume of timber is determined from a physical characteristic determined from a rendered 2-dimensional (2D) stitched image or 3D image of the load, distance data, and robot position data.

17. A method for taking physical measurements from a load on a vehicle, the load comprising a first packet of logs and a second packet of logs, and the load having dimensions of load length, load width, and load height, the method comprising:
(a) providing a load scanning apparatus, the load scanning apparatus comprising:
(i) a scanning robot comprising:
a cross member to which an array of sensors is coupled,
wherein the array of sensors is fixed relative to each other in a first direction and are configured to move together in a second direction in a scanning plane, wherein the array of sensors is positioned to have a line of sight perpendicular to the scanning plane relative to at least log ends of the first packet of logs, wherein the array of sensors spans across at least one dimension of the load in the first direction, wherein the array of sensors is configured to capture a collection of images of the load from the scanning plane, and configured to capture distance information about a distance of the load from the scanning plane, and at least one of:
the cross member moves between a raised position and a lowered position on the scanning robot to scan the load, and
the cross member has a width configured to fit in a gap between:
the first packet of logs, and
the second packet of logs; and (ii) a processor configured to:
process the collection of images taken by the array of sensors, and
stitch the collection of images together to generate a 3-dimensional (3D) representation of the load;

(b) positioning the load in a load receiving bay of the load scanning apparatus;

(c) moving the array of sensors together; and (d) taking a collection of images, using the scanning robot, from the load; and (e) determining, based on the collection of images, physical measurements of the load using the processor.

18. The method of claim 17, wherein:
the array of sensors is configured to move to a first vertical height relative to protruding or recessed log ends of the first packet of logs; and
the array of sensors is configured to perpendicularly capture images of protruding or recessed log ends of the first packet of logs at the first height.

19. The method of claim 17, wherein the array of sensors moves between the raised position and the lowered position to capture the collection of images of the load at a horizontal plane substantially perpendicular to log ends of at least the first packet of logs.

20. The method of claim 17, wherein the cross member has a width between 30 mm and 500 mm.

* * * * *